(12) United States Patent
Osswald et al.

(10) Patent No.: US 6,395,256 B1
(45) Date of Patent: May 28, 2002

(54) ADENOSINE DETECTION IN SMALL SAMPLES

(75) Inventors: Hartmut Osswald, Am Apfelberg 10, 13-72076 Tubingen; Doris Kloor, Boblingen, both of (DE)

(73) Assignee: Hartmut Osswald, Tubingen (DE)

( * ) Notice: Subject to any disclaimer, the term of this patent is extended or adjusted under 35 U.S.C. 154(b) by 0 days.

(21) Appl. No.: 09/582,150

(22) PCT Filed: Dec. 18, 1998

(86) PCT No.: PCT/EP98/08314

§ 371 (c)(1), (2), (4) Date: Jun. 21, 2000

(87) PCT Pub. No.: WO99/34210

PCT Pub. Date: Jul. 8, 1999

(30) Foreign Application Priority Data

Dec. 23, 1997 (DE) .......................................... 197 57 571

(51) Int. Cl.⁷ ........................ A61K 51/00; A61M 36/14
(52) U.S. Cl. .................... 424/1.69; 424/1.11; 424/1.65; 424/1.73; 424/9.3; 424/9.1; 536/276; 435/18
(58) Field of Search ................................. 424/9.1, 1.11, 424/1.65, 9.3, 9.4, 9.5, 9.6, 9.7, 9.8, 1.73; 206/223, 569, 570; 536/27.6; 435/4, 7.1, 18

(56) References Cited

U.S. PATENT DOCUMENTS 5,827,645 A * 10/1998 Sundrehagen .................. 435/4

OTHER PUBLICATIONS

Kloor et al (1996, abstract), Kidney Blood Pressure Res., vol. 19, No. 2, pp. 100–108.*

"Simple And Sensitive Binding Assay Of Measurement Of Adenosine Using Reduced S–Adenosylhomocysteine Hydrolase", Kloor, 1996., Clinical Chemistry, vol. 46, No. 4, pp. 537–542.

* cited by examiner

Primary Examiner—Dameron L. Jones
(74) Attorney, Agent, or Firm—Merchant & Gould P.C.

(57) ABSTRACT

The invention relates to a method for detecting adenosine with the inactive S-adenosyl homocysteine hydrolase's enzyme which selectively and only binds adenosine with high affinity. The inventive method enables adenosine to be determined in small sample volumes without the need for additional purification of said sample.

6 Claims, No Drawings

ADENOSINE DETECTION IN SMALL SAMPLES

This application is a 371 of PCT/EP 98/08314 Filed Dec. 18, 1998.

The present invention concerns a simple and sensitive assay for measurement of adenosine in small samples using definite concentrations of reduced S-adenosylhomocysteine (SAH) hydrolase and radioactive adenosine. The SAH hydrolase-adenosine complex is separated preferably by a filtration equipment and the radioactive adenosine incorporated in this SAH hydrolase-adenosine complex is measured by scintillation counting.

A further objective of the invention is the combination of the analytical substances required for the assay.

Adenosine is an endogenous nucleoside that interacts in various physiological processes which are also regulated by hormones and neurotransmitters. Adenosine actions are mediated by stimulation of specific cell surface receptors which are found to be ubiquitous in mammals.

In the cytosol hydrolysis of AMP leads to adenosine by the activity of endo-5'-nucleotidase. Another source of adenosine generation is the hydrolysis of SAH to adenosine and homocysteine by SAH hydrolase. Adenosine, a product of the energy metabolismn, functions as a mediator in the metabolic control of organ function in heart, kidney and brain. Current research in biochemistry, pharmacology, physiology and clinical chemistry is carried out with the aim to investigate the physiological role and therapeutical potency of adenosine and several adenosine derivates in terms of treating diseases in which adenosine metabolism is deranged and thus organ function impaired. The methods available for measurement of adenosine are:

1. Photometrical Detection

The reduction of adenosine concentration is measured photometrically at 265 nm in the presence of adenosine deaminase. The disavantage of this method is the requirement of sample purification prior measurement to remove purine compounds and other endogenous substances. The detection limit for adenosine is $10^{-7}$ mol/l.

2. High pressure Liquid Chromatography (HPLC)

The HPLC method combines separation of adenosine and its photometrical detection of adenosine at 254 nm. This method, however, has its limitation with respect to sufficient separation of several interfering nucleotides. In addition, the sensitivity to detect adenosine at 0.3 µmol/l is to low for small samples volume.

3. Radioimmunoassay

This method is based on an antibody method with adenosine 2', 3'-O-disuccinyl-3-[$^{125}$I]-Iodtyrosin methyl ester as tracer and with an antibody against disuccinylated-adenosine. For this method a sample purification is not required but adenosine in each sample must be coupled to 2',3'-O-disuccinyl-3-[$^{125}$I]-Iodtyrosin. The detection limit is more sensitive ($6 \cdot 10^8$ mol/l) when compared with the photometric or HPLC methods.

The subject of the invention is correspondingly a sensitive method suitable for detection of adenosine in small sample of 10 µl or biopsies of 2–10 mg tissue without purification of deproteinized samples.

The subject of the invention was resolved by an assay for measurement of adenosine in small samples using reduced SAH hydrolase and radioactive adenosine in definite concentrations. The SAH hydrolase-adenosine complex was separated preferably by a filtration equipment e.g. filtration apparatus for separation of reaction mixtures (DE 197 49 929 A1). The radioactivity incorporated in this complex was measured by scintillation counting.

The further subject of the invention is the largely improved ability of the reduced form of the enzyme SAH hydrolase to bind adenosine with high affinity.

The following table 1 demonstrates that the reduced enzyme is able to bind adenosine with high affinity. The table 1 also discloses that several substances that bind to the active form of the enzyme have a much lower affinity to the reduced form of the enzyme.

TABLE 1

$EC_{50}$ values of $^3$H-adenosine displacement using active and reduced SAH hydrolase. $EC_{50}$ values are expressed in nmol/l.

| Adenosine Analoga | active SAH hydrolase | reduced SAH hydrolase |
|---|---|---|
| adenosine | 57 | 24 |
| cAMP | 104 | >100000 |
| adenine | 11500 | >100000 |
| 2'-deoxyadenosine | 94 | 630 |
| SAH | 246 | 400 |
| homocysteine | 5000 | 5000 |
| AMP | 10000 | 100000 |
| ADP | 10000 | >100000 |
| AMP | 10000 | >100000 |
| inosine | 10000 | 10000 |
| diadenosine-diphosphate | 138 | 10000 |
| diadenosine-dialdehyde | 180 | 10000 |
| NECA | 240 | >100000 |
| theophylline | >100000 | >100000 |

The particular advantage of the new invention is that the reduced enzyme retains its ability to bind adenosine with high affinity ($K_D 2 \cdot 10^{-8}$ mol/l). Since interferences of endogenous substances with the binding of radioactive adenosine are no longer present, no sample purification is necessary to measure adenosine in deproteinized samples.

The following example is given for the purpose of illustrating the invention:

SAH hydrolase is purified with classical chromatographical methods to homogeneity from organs e.g. from bovine kidney. Fresh bovine kidney (450 g), obtained from the local slaughterhouse were homogenized in two volumes of 50 mM potassium phosphate buffer pH 7.0, 1 mM DTT, 1 mM EDTA and 10 mM PMSF. The homogenate was centrifuged at 20000×g for 60 min. Ammonium sulfate (164 g/l) was added to the supernatant. After centrifugation at 20000×g for 30 min the precipitate was disolved in 300–400 ml 20 mM Tris/HCl pH 7.5, 1 mM DTT and 1 mM EDTA and dialyzed against the same buffer.

Chromatography

1. DEAE Sepharose Fast Flow

The dialyzed enzyme solution was applied onto a column (5×25 cm) of DEAE Sepharose® Fast Flow equilibrated with the dialysis buffer. The column was washed with 1700 ml of the same buffer and the enzyme was eluted by a 2000 ml linear gradient of 0 to 0.4 M KCl in 20 mM Tris/HCl pH 7.5, 1 mM DTT and 1 mM EDTA. Active fractions were eluted between 250 and 350 mM KCl (flow rate 10 ml/min) pooled and dialyzed against 50 mM potassium phosphate buffer pH 6.8, 1 mM DTT and 1 mM EDTA.

2. Hydroxylapatite

The dialyzed enzyme solution was then applied onto a column of hydroxylapatite (5×10 cm) equilibrated with 50 mM potassium phosphate pH 6.8, 1 mM DTT, 1 mM EDTA. SAH hydrolase remained in the unadsorbed fractions, which were combined and dialyzed against 10 mM potassium phosphate buffer pH 6.8 (flow rate 1.5 ml/min).

Aminohexyl Sepharose

The dialyzed fractions from the previous step were applied onto a EAH-Sepharose 4B column (2.6×10 cm)

equilibrated with 10 mM potassium phosphate buffer pH 6.8. The column was washed with 200 ml of the same buffer, and the enzyme was eluted by a linear gradient of 0 to 0.4 M KCl in 10 mM potassium phosphate buffer pH 6.8. The SAH hydrolase fractions were eluted between 120 and 200 mM KCl, were pooled and concentrated by an AMICON protein concentrater to a small volume of 3–5 ml.

Superdex™ 200 Gelfiltration

The concentrated SAH-hydrolase solution was chromatographed on a column of Superdex™ 200 (2.6×60 cm) equilibrated with phosphate buffer saline pH 7.4, 1 mM DTT and 1 mM EDTA. Fractions containing SAH hydrolase were pooled, the protein concentration determined and stored at −20° C. until use.

The purity of the isolated enzyme was determined by SDS-polyacrylamidgradient gel electophoresis. From a 600 g weighty bovine kidney 30 mg pure SAH hydrolase could be prepared. The exchange of $NAD^+$ by NADH results in a totally inactive enzyme.

Active SAH hydrolase can be inactivated by three different methods:

1. The tightly bound $NAD^+$ of the active enzyme is removed by incubation with 150 mM NaCl, 8 mM ATP and 8 mM $MgCl_2$ for 90 min at 37° C. The enzyme solution was dialyzed and the resulted apo-enzyme is completely inactive and loses its binding affinity to adenosine. The reconstitution of the apo-enzyme with 1 mM NADH for 90 min at room temperature resulted in an enzymatically inactive enzyme with high adenosine binding capacity.
2. The enzymatically active enzme is incubated with 2 volumes of saturated ammonium sulfate for 60 min at room temperature or at 0° C. The solution is centrifuged at 12000×g for 30 min and the precipitate is dissolved in 20 mM TrisHCl pH 7.0 and dialyzed against the same buffer for 6 h. The apo-enzyme is reconstituted with 1 mM NADH for 90 min at room temperatur. The NADH-SAH hydrolase is enzymatically inactive, yet, its adenosine binding capacity is retained.
3. The enzymatically active enzyme is incubated with 100 $\mu$M azido-adenosine at room temperature for 2 h. Thereafter the mixture is irradiated for 5 min using UV at 254 nm. The covalent photolabeling of azido-adenosine on SAH hydrolase results in a complete inactivation of the enzyme. The reduced SAH hydrolase retains its ability to bind adenosine with high capacity.

During the reduction procedure of SAH hydrolase, independent of the method used, about 25% of total protein (corresponding 7.5 mg) gets lost. The inactive ezyme (2 mg/ml) is stable at 4° C. in 20 mM Tris, 40 mM Hepes pH 7.0 for at least 4 weeks and at −20° C. for at least 2 month. Lyophylized enzyme (2 mg/ml) is stable at −20° C. for 2 month. The production of inactive SAH hydrolase from one bovine kidney is sufficient to carry out 20000 measurements of adenosine.

Quantification of Adenosine by Displacement from its Binding Site

The adenosine concentration is determined by displacement experiments. The adenosine of the samples displaces the radioactive adenosine from the binding site of the reduced SAH hydrolase molecule.

The displacement of radioactive adenosine is performed in a final assay volume of 300 $\mu$l containing the components as follows:

100 $\mu$l reduced SAH hydrolase (1 $\mu$g/300 $\mu$l)

50 $\mu$l $^3$H-adenosine (1 pmol/300 $\mu$l) specific activity 54.5 Ci/mmol

100 $\mu$l sample

50 $\mu$l buffer—20 mM Tris, 40 mM Hepes pH 7.0

The equilibrium of adenosine binding to reduced enzyme is reached at room temperature after 10 h. Therefore the samples are incubated over night. The assay mixture is separated through nitrocellulose filters with a filtration equipment. The radioactive adenosine-enzyme-complex absorbed on the filters is determined by liquid scintillation counting.

To construct a standard curve, the log values of the adenosine concentrations are plotted against the $^3$H-adenosine bound (%) and the data resulted in a typical sigmoidal concentration-response curve. The adenosine values between $10^{-9}$ and $10^{-7}$ mol/l from the resulting curve is then used to calculate the adenosine values of samples on the basis of their counts per minutes observed.

Since adenosine has a high affinity to the inactive enzyme and radioactive $^3$H-adenosine is used as tracer according to the invention the detection limit for adenosine in this assay is $10^{-9}$ mol/l or 3 pmol/sample.

This assay is an attractive alternative to HPLC in routine and research laboratories when only small sample volumes are available and a high sensitivity of the method is necessary. Further application of this analytical method are radiocontrast media examinations and renal allographs transplantation as a diagnostic tool to monitor renal function in transplanted patients.

The following example is given for the combination of the analytical substances according to the invention for determination of adenosine in small samples.

Content of Adenosine Assay-kit:

[2,8,5'-$^3$H]-adenosine 110 pmol (lyophylized)

reduced SAH hydrolase 110 $\mu$g (lyophylized)

adenosine 16.5 mg (pulv.)

activated charcoal 2 g (pulv.)

dextran 1 g (pulv.)

20 mM Tris/HCl buffer pH 7.0 100 ml concentrate 2× (liquid)

According to the invention [2,8,5'-$^3$H]-adenosine and the reduced SAH hydrolase are reconstituted with 20 mM Tris/HCl buffer pH 7.0. The 16.5 mg adenosine are used to made a 6 mM adenosine solution which is further diluted for the calibration curve. The concentrations in the assay samples are of 1, 10, 25, 50, 75, 100, 150 nM.

Activated charcoal and dextran are used for a 0.6% activated charcoal and a 0.2% dextran solution in 20 mM Tris/HCl buffer pH 7.0.

The enyzme-ligand-complex is separated by filtration.

The unbound ligand could also be removed from the enzyme-ligand-complex by the addition of 1 ml activated charcoal and dextran solution to the assay sample following centrifugation.

For the analytical determination 100 $\mu$l [2,8,5'-$^3$H]-adenosine, 100 $\mu$l reduced SAH hydrolase and 100 $\mu$l sample or unlabeled adenosine for the calibration curve are used.

What is claimed is:

1. A method for the detection of adenosine in fluids comprising the steps:

a) adding to a sample in which adenosine has to be determinated a definite concentration of reduced S-adenosylhomocysteine hydrolase and radioactive adenosine:

b) separating the S-adenosylhomocysteine hydrolase-adenosine-complex;

c) measuring the radioactivity incorporated in the enzyme-adenosine complex is by scintillation counting.

2. A method according to claim 1, characterized in that the labelling of adenosine is radioactive or fluorescent.

3. A method according to claim 1 further comprising measuring adenosine in fluids of patients undergoing examinations with radio contrast media.

4. A method according to claim 1 further comprising monitoring adenosine in isolated organs or cell culture.

5. A kit of analytic substances for the determination of adenosine in fluids containing [2,8,5'-$^3$H]-adenosine, reduced S-adenosylhomocysteine hydrolase, adenosine, activated charcoal and dextran.

6. The kit of analytic substances according to claim 5 containing 110 pmol [2,8,5'-$^3$H]-adenosine, 110 μg reduced S-adenosylhomocysteine hydrolase, 16.5 mg adenosine, 2 g activated charcoal, 1 g dextran and 100 ml (2×concentrate) 20 mM Tris/HCl pH 7.0.

* * * * *